(12) United States Patent
Dasseux

(10) Patent No.: US 6,455,088 B1
(45) Date of Patent: *Sep. 24, 2002

(54) PEPTIDE/LIPID COMPLEX FORMATION BY CO-LYOPHILIZATION

(76) Inventor: Jean-Louis Dasseux, 7898 Huron Oak Dr., Brighton, MI (US) 48116

( * ) Notice: Subject to any disclaimer, the term of this patent is extended or adjusted under 35 U.S.C. 154(b) by 0 days.

This patent is subject to a terminal disclaimer.

(21) Appl. No.: 09/642,363

(22) Filed: Aug. 21, 2000

Related U.S. Application Data

(63) Continuation of application No. 08/942,597, filed on Oct. 2, 1997, now Pat. No. 6,287,590.

(51) Int. Cl.$^7$ .............................................. A61K 9/127
(52) U.S. Cl. .............................. 426/450; 514/2; 514/12; 514/13
(58) Field of Search ........................... 426/450; 264/4.1, 264/4.3, 4.6; 514/2, 21, 12, 13

(56) References Cited

U.S. PATENT DOCUMENTS

| | | | |
|---|---|---|---|
| 4,229,360 A | | 10/1980 | Schneider et al. |
| 4,411,894 A | | 10/1983 | Schrank et al. |
| 4,508,703 A | | 4/1985 | Redziniak et al. |
| 4,857,319 A | | 8/1989 | Crowe et al. |
| 4,880,635 A | | 11/1989 | Janoff et al. |
| 5,077,057 A | * | 12/1991 | Szoka |
| 5,178,875 A | * | 1/1993 | Lenk |
| 5,652,339 A | * | 7/1997 | Lerch |
| 5,698,677 A | * | 12/1997 | Eibl |
| 5,756,069 A | | 5/1998 | Torchilin et al. |
| 5,766,625 A | | 6/1998 | Schreier et al. |
| 5,785,984 A | | 7/1998 | Kurihare et al. |

FOREIGN PATENT DOCUMENTS

| | | | |
|---|---|---|---|
| EP | 0087993 | * | 9/1983 |
| EP | 0087993 | | 4/1985 |

OTHER PUBLICATIONS

Brouillette and Anantharamaiah, 1995, "Structural models of human apolipoprotein A–I," *Biochim. Biophys. Acta* 1256:103–129.

Deamer et al., 1983, *Liposomes* (Ostro, Ed.), Marcel Dekker, Inc., New York.

Dufourcq et al., 1986, "Morphological changes of phosphatidylcholine bilayers induced by melittin: vesicularization, fusion, discoidal particles," *Biochim. Biophys. Acta* 859:33–48.

Hope et al., 1986, "Generation of multilamellar and unilamellar phospholipid vesicles," *Chemistry and Physics of Lipids* 40:89–107.

Johnson et al., 1971, "Single bilayer liposomes," *Biochim. Biophys. Acta* 233:820.

Jonas, 1986, "Reconstitution of High–Density Lipoproteins," *Meth. Enz.* 128:553–582.

Jonas, 1992, "Lipid–Binding Properties of Apolipoproteins," *Structure and Function of Apolipoproteins*, CRC Press, Ch. 8, pp. 217–250.

Knott et al., 1985, "Human Apolipoprotein B: Structure of Carboxyl–Terminal Domains, Sites of Gene Expression, and Chromosomal Localization," *Science* 230:37–43.

Lins et al., 1993, "Enzymatic hydrolysis of reconstituted dimyristoylphosphatidylcholine–apo A–I complexes," *Biochim. Biophys. Acta* 1151:137–142.

(List continued on next page.)

Primary Examiner—Gollamudi S. Kishore
(74) *Attorney, Agent, or Firm*—Pennie & Edmonds LLP

(57) ABSTRACT

The invention relates to the formation of peptide/lipid vesicles and complexes through the co-lyophilization of peptides, preferably that are able to adopt an amphipathic alphahelical conformation, and one or more lipids. A single solution which solubilizes both the peptides and lipids or two separate solutions may be lyophilized.

27 Claims, 8 Drawing Sheets-

OTHER PUBLICATIONS

Figure 1:
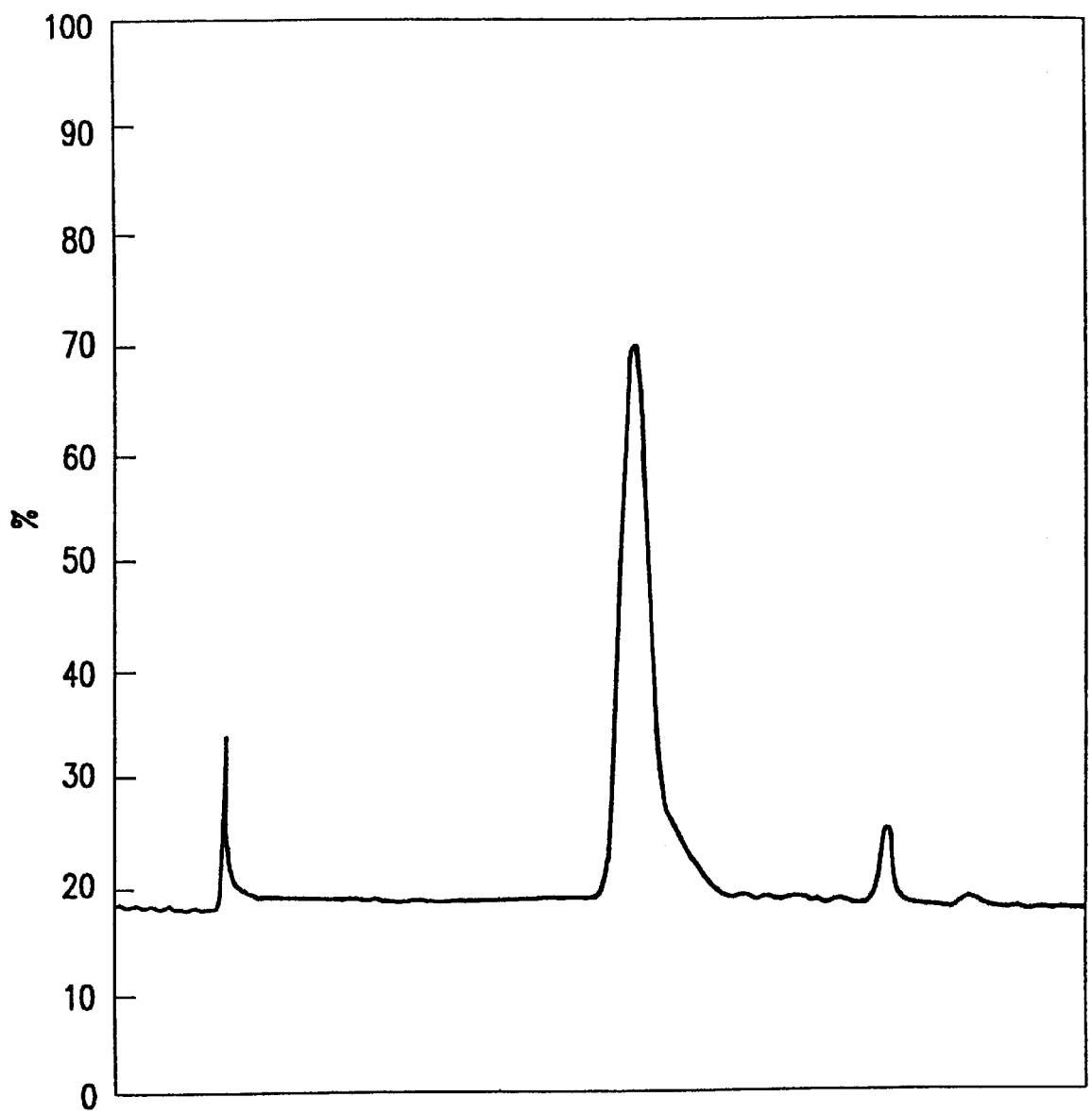

Nedelec et al., 1989, "Comparative study of myelin proteolipid apoprotein solvation by multilayer membranes of synthetic DPPC and biological lipid extract from bovine brain. An FT–IR investigation," *Biochimie* 71:145–151.

Segrest, 1976, "Molecular packing of high density lipoproteins: a postulated functional role," *FEBS Lett.* 69(1):111–114.

Subbarao et al., 1988, "Lecithin: Cholesterol Acyltransferase Activation by Synthetic Amphipathic Peptides," *Proteins*, 3:187–198.

Segrest et al., 1994, "The Amphipathic α–helix: A Multifunctional Structural Motif in Plasma Apolipoproteins," *Adv. Protein Chem*, 45:303–369.

Epand et al., 1995, "Mechanisms for the Modulation of Membrane Bilayer Properties by Amphipathic Helical Peptides," *Biopolymers* (Peptide Sciences), 37:319–338.

Segrest et al., 1974, "A Molecular Theory of Lipid–Protein Interactions in the Plasma Lipoproteins," *FEBS Letters*, 38(3):247–253.

Pons et al., 1993, "Liposomes obtained by the ethanol injection method," *Int. J. Pharm.* 95: 51–56.

Anantharamaiah et al., 1985, "Studies of Synthetic Peptide Analogs of the Amphipathic Helix," The Journal of Biological Chemistry 260, No. 18:10248–10255.

Anantharamaiah et al., 1990, "Role of Amphipathic Helixes in HDL Structure/Function," In Hypercholesterolemia, Hypocholesterolemia, Hypertriglyceridemia, In Vivo Kinetics from the series *Advances in Experimental Medicine and Biology*, ed. Malmendiers et al., Plenum Press, vol. 285, pp. 131–140.

Hendry et al., 1985, "Further Evidence that Membrane Thickness Influences Voltage–Gated Sodium Channels," Biophysical Journal 47: 841–845.

Segrest, 1977, "Amphipathic Helixes and Plasma Lipoproteins: Thermodynamic and Geometric Considerations," Chemistry and Physics of Lipids 18: 7–22.

Segrest and Feldmann, 1977, "Amphipathic Helixes and Plasma Lipoproteins: A Computer Study," Biopolymers 16: 2053–2065.

Segrest et al., 1990, " Amphipathic Helix Motif: Classes and Properties," Proteins: Structure, Function, and Genetics 8: 103–117.

Segrest et al., 1983, "Studies of Synthetic Peptide Analogs of the Amphipathic Helix," The Journal of Biological Chemistry 258: 2290–2295.

Segrest et al., 1992, "The Amphipathic Helix in the Exchangeable Apolipoproteins: A Review of Secondary Structure and Function," Journal of Lipid Research 33: 141–166.

Spuhler et al., 1994, "Binding of Apoliprotein A–I Model Peptides to Lipid Bilayers," The Journal of Biological Chemistry 269: 23904–23910.

* cited by examiner

US 6,455,088 B1

PEPTIDE/LIPID COMPLEX FORMATION BY CO-LYOPHILIZATION

This is a continuation of application Ser. No. 08/942,597, filed Oct. 2, 1997, now U.S. Pat. No. 6,287,590.

1. FIELD OF THE INVENTION

The invention relates to the formation of peptide/lipid vesicles and complexes through the co-lyophilization of peptides, preferably that are able to adopt an amphipathic alpha-helical conformation, and one or more lipids. A single solution which solubilizes both the peptides and lipids or a two separate solutions may be lyophilized. The methods are used to generate stable peptide/lipid vesicles and complexes including but not limited to micellar, spherical and discoidal complexes in bulk preparations and in smaller units, as may be suitable for dosages.

2. BACKGROUND OF THE INVENTION

Liposomes are vesicles composed of at least one lipid bilayer membrane enclosing an aqueous core. Generally, phospholipids comprise the lipid bilayer, but the bilayer may be composed of other lipids. The aqueous solution within the liposome is referred to as the "captured volume." Liposomes have been developed as vehicles to deliver drugs, cosmetics, bioactive compounds among other applications. The lipid bilayer encapsulates the drug, cosmetic, bioactive compound, and the like, within the captured volume of the liposome and the drug is expelled from the liposome core when the lipid bilayer comes in contact with a cell surface membrane. The liposome releases its contents to the cell by lipid exchange, fusion, endocytosis, or adsorption. Ostro et al., 1989, *Am. J. Hosp. Pharm.* 46:1576. Alternatively, the drug, cosmetic, bioactive compound and the like could be associated with or inserted into the lipid bilayer membrane of the vesicle.

In addition to vesicles, lipid-containing complexes have been used to deliver agents in particle form. For instance, many researchers have found it useful to prepare reconstituted lipoprotein-like particles or complexes which have similar size and density as high density lipoprotein (HDL) particles. These reconstituted complexes usually consist of purified apoproteins (usually apoprotein A-1) and phospholipids such as phosphatidylcholine. Sometimes unesterified cholesterol is included as well. The most common methods of preparing these particles are (1) co-sonication of the constituents, either by bath sonication or with a probe sonicator, (2) spontaneous interaction of the protein constituent with preformed lipid vesicles, (3) detergent-mediated reconstitution followed by removal of the detergent by dialysis. Jonas, 1986, *Meth. in Enzymol.* 128:553–582; Lins et al., 1993, *Biochimica et Biophysica Acta*, 1151:137–142; Brouillette & Anantharamaiah, 1995, *Biochimica et Biophysica Acta*, 1256:103–129; Jonas, 1992, *Structure & Function of Apoproteins*, Chapter 8:217–250. Similar complexes have also been formed by substituting amphipathic helix-forming peptides for the apoprotein components. Unfortunately, each of these methods presents serious problems for the formation of large amounts of pure complexes on a reasonably cost-effective basis. Further, none of these publications disclose the co-lyophilization of peptides/or peptides analogues which are able to adopt an amphipathic alpha helical conformation and a lipid.

A range of technologies is known for producing lipid vesicles and complexes. Vesicles, or liposomes, have been produced using a variety of protocols, forming different types of vesicles. The various types of liposomes include: multilamellar vesicles, small unilamellar vesicles, and large unilamellar vesicles.

Hydration of phospholipids (or other lipids) by aqueous solution can also result in the dispersion of lipids and spontaneous formation of multimellar vesicles ("MLVs"). An MLV is a liposome with multiple lipid bilayers surrounding the central aqueous core. These types of liposomes are larger than small unilamellar vesicles (SUVS) and may be 350–400 nm in diameter. MLVs were originally prepared by solubilizing lipids in chloroform in a round-bottom flask and evaporating the chloroform until the lipid formed a thin layer on the wall of the flask. The aqueous solution was added and the lipid layer was allowed to rehydrate. Vesicles formed as the flask is swirled or vortexed. Deamer et al., 1983, in *Liposomes* (Ostro, Ed.), Marcel Dekker, Inc. New York (citing Bangham et al., 1965, *J. Mol. Biol.* 13:238). Johnson et al. subsequently reported that this method also generated single lamellar vesicles. Johnson et al., 1971, *Biochim. Biophys. Acta* 233:820.

A small unilamellar vesicle (SUV) is a liposome with a single lipid bilayer enclosing an aqueous core. Depending on the method employed to generate the SUVS, they may range in size from 25–110 nm in diameter. The first SUVs were prepared by drying a phospholipid preparation in chloroform under nitrogen, adding the aqueous layer to produce a lipid concentration in the millimolar range, and sonicating the solution at 45° C. to clarity. Deamer et al., 1983, in *Liposomes* (Ostro, Ed.), Marcel Dekker, Inc. New York. SUVs prepared in this fashion yielded liposomes in the range of 25–50 nm in diameter.

Another method of making SUVs is rapidly injecting an ethanol/lipid solution into the aqueous solution to be encapsulated. Deamer et al., 1983, in *Liposomes* (Ostro, Ed.), Marcel Dekker, Inc. New York (citing Batzri et al., 1973, *Biochim. Biophys. Acta* 298:1015). SUVs produced by this method range in size from 30–110 nm in diameter.

SUVs may also be produced by passing multilamellar vesicles through a French Press four times at 20,000 psi. The SUVs produced will range in size from 30–50 nm in diameter. Deamer et al., 1983, in *Liposomes* (Ostro, Ed.), Marcel Dekker, Inc. New York (citing Barenholz et al., 1979, FEBS Letters 99:210).

Multilamellar and unilamellar phospholipid vesicles can also be formed by extrusion of aqueous preparations of phospholipids at high pressure through small-pore membranes (Hope et al., 1996, *Chemistry and Physics of Lipids*, 40:89–107)

A large unilamellar vesicle (LUV) is similar to SUVs in that they are single lipid bilayers surrounding the central aqueous core, but LUVs are much larger that SUVs. Depending on their constituent parts and the method used to prepare them, LUVs may range in size from 50–1000 nm in diameter. Deamer et al., 1983, in *Liposomes* (Ostro, Ed.), Marcel Dekker, Inc. New York. LUVs are usually prepared using one of three methods: detergent dilution, reverse-phase evaporation, and infusion.

In the detergent dilution technique, detergent solutions such as cholate, deoxycholate, octyl glucoside, heptyl glucoside and Triton X-100 are used to form micelles from the lipid preparation. The solution is then dialyzed to remove the detergent and results in the formation of liposomes. Deamer et al., 1983, in *Liposomes* (Ostro, Ed.), Marcel Dekker, Inc. New York. This method is time consuming and removal of the detergent is generally incomplete. The presence of detergent in the final preparation may result in some toxicity of the liposome preparation and/or modification of the physicochemical properties of the liposome preparation.

The reverse-phase evaporation technique solubilizes lipid in aqueous-nonpolar solutions, forming inverted micelles. The nonpolar solvent is evaporated and the micelles aggregate to form LUVs. This method generally requires a great deal of lipid.

The infusion method injects a lipid solubilized in a non-polar solution into the aqueous solution to be encapsulated. As the nonpolar solution evaporates, lipids collect on the gas/aqueous interface. The lipid sheets form LUVs and oligolamellar liposomes as the gas bubbles through the aqueous solution. Liposomes are sized by filtration. Deamer et al., 1983, in *Liposomes* (Ostro, Ed.), Marcel Dekker, Inc. New York (citing Deamer et al., 1976, *Biochim. Biophys. Acta* 443:629 and Schieren et al., 1978, *Biochim. Biophys. Acta* 542:137). Infusion procedures require a fairly high temperature for infusion and may have a relatively low encapsulation efficiency. Deamer et al., 1983, in *Liposomes* (Ostro, Ed.), Marcel Dekker, Inc. New York It is has been a goal of liposome research to develop liposome preparations that may be stored for long periods of time before use. For example, U.S. Pat. No. 4,229,360 to Schneider et al., discloses a method of dehydrating liposomes by adding a hydrophilic compound to a colloidal dispersion of liposomes in an aqueous liquid and dehydrating the solution, preferably by lyophilization. Examples of hydrophilic compounds are high molecular weight hydrophilic polymers or low molecular weight compounds such as sucrose.

U.S. Pat. No. 4,411,894 to Shrank et al., discloses the use of high concentrations of sucrose in sonicated preparations of liposomes. The liposomes contain fat-soluble products in the captured volume, although the preparations could be lyophilized, the method could not prevent the loss of a significant amount of the captured contents despite the high concentration of sucrose.

Crowe et al., U.S. Pat. No. 4,857,319 disclosed the use of disaccharides such as sucrose, maltose, lactose and trehalose to stabilize liposomes when liposomes are freeze dried. The amount of disaccharide with respect to the lipid content of the component (w/w) is within 0.1:1 to 4:1. Crowe achieved greater success in preserving liposomal integrity using this method than that afforded by the method disclosed by Shrank in U.S. Pat. No. 4,441,894.

Janoff et al, U.S. Pat. No 4,880,635 disclose a method for dehydrating liposomes in which liposomes were lyophilized in the presence of protective sugars such as trehalose and sucrose, preferably on both the inner and outer leaflets of the lipid bilayer. Sufficient water is retained in the method of Janoff et al. so that rehydration of the dried liposomes yields liposomes with substantial structural integrity.

However, there is a need in the art for a simple and cost effective method of forming lyophilized peptide/lipid complexes which may be then be rehydrated. The method of the present invention yields peptide/lipid mixtures in a stable, lyophilized powder which may be stored, used as a powder, or used after rehydration to form peptide/lipid complexes.

3. SUMMARY OF THE INVENTION

The invention is a method for preparing peptide or protein-(phospho)lipid complexes or vesicles which may have characteristics similar to high density lipoprotein (HDL). The method utilizes a solvent system in which at least one peptide is solubilized in one solution, and at least one lipid is solubilized in another solution. The two solutions are selected such that they are miscible with one another. The solutions are then combined, and the resulting solution is lyophilized.

The method also may be practiced by a second type of solvent system comprising a solution into which both the protein or peptide and the lipid may be solubilized. This solution may be a single solution, or may be a composite solution made by combining two or more solutions before the addition of peptides and lipids. Peptides and lipids are solubilized in the solution or composite solution and the peptide/lipid solution is then lyophilized.

Preferably, the peptides of the present invention are peptides which are able to adopt an amphipathic helical conformation. In one specific embodiment of the invention, the peptide is a lipid binding protein. In other embodiment, peptide analogues of ApoA-I, ApoA-II, ApoA-IV, ApoC-I, ApoC-II, ApoC-III, ApoE, other apolipoprotein analogues and the like are utilized in place of or in combination with the peptides. In another specific embodiment, the method is used to prepare ApoA1 analogue/(phospho)lipid complexes similar to HDL. The ApoA1/lipid complexes are useful in treating disorders associated with dyslipoproteinemias including but not limited to hypercholesterolemia, hypertriglyceridemia, low HDL, and apolipoprotein A-1 deficiency, septic shock, for in vitro diagnostic assays as markers for HDL populations, and for use with imaging technology.

The method of the invention enables the preparation of peptide/lipid complexes for parenteral administration including but not limited to intravenous, intraperitoneal, subcutaneous, intramuscular, and bolus injections to animals or humans. Further, the peptide/lipid complexes can also be formulated for oral, rectal, mucosal (e.g. oral cavity) or topical administration to animals or humans, or for in vitro experimentation.

The method may be used for large scale production of amphipathic peptide/phospholipid complexes, lipid binding protein/phospholipid complexes, and/or ApoA1 peptide analogue/phospholipid complexes. The lyophilized material may be prepared for bulk preparations, or alternatively, the mixed peptide/lipid solution may be apportioned in smaller containers (for example, single dose units) prior to lyophilization, and such smaller units may be prepared as sterile unit dosage forms.

The lyophilized powder prepared by the method of the invention can be rehydrated into a particulate-free sterile solution immediately before injection, or alternatively, the lyophilized powder can be formulated into an appropriate solid dosage form and administered directly.

The method may also be suitable for storage of compounds which may be otherwise unstable or insoluble in the absence of lipids.

The method may be used for the formulation of products for the treatment or prevention of human diseases, including such applications as co-presentation of antigens in vaccines, treatment or prevention of dyslipoproteinemias, including but not limited to hypercholesterolemia, hypertriglyercidemia, low HDL, and apolipoprotein A-1 deficiency, cardiovascular disease such as atherosclerosis, septic shock, or infectious diseases.

The method may be used for the preparation of complexes that could be used as carriers for drugs, as vectors (to deliver drugs, DNA, genes), for example, to the liver or to extra-hepatic cells, or as scavengers to trap toxin (e.g. pesticides, LPS, etc.).

3.1. Definitions

As used herein, a "solvent system" refers to one or more solvents which are capable of solubilizing peptides and/or lipids and, if more than one, which are miscible with one another.

As used herein, "peptide/lipid complexes" refers to an aggregation of lipid moieties and peptides forming particles within the size range of high density lipoproteins (HDLs).

As used herein, "co-lyophilized" refers to the lyophilization, freeze-drying, or vacuum drying of more than one compound (e.g., peptide, protein, lipid, phospholipid) in solution in the same vessel. For example, a lipid solution may be combined with a peptide solution in the same vessel and the resulting combination of solutions is lyophilized together, thereby lyophilizing the peptides and lipids simultaneously.

As used herein "amphipathic peptide" or "amphipathic alpha helical peptides" means peptides which are able to adopt an amphipathic or amphipathic helical conformation, respectively. The amphipathic alpha helix is an often encountered secondary structural motif in biologically active peptides and proteins. See *AmphiPathic helix motif: classes and properties* by Jere P. Segrest, Hans de Loof, Jan G. Dohlman, Christie G. Brouillette, and G. M. Ananthamaiah. *PROTEINS: Structure Functions and Genetics* 8:103–117 (1990). An amphipathic alpha helix is an alpha helix with opposing polar and nonpolar faces oriented along the long axis of the helix. A specific distribution of charged residues is evident along the polar face. Amphipathic helices, as defined, are complementary for the polar-nonpolar interface of hydrated bulk phospholipid; these lipid-associating domains have been postulated to interact with the phospholipid by partially immersing themselves at the interface between the fatty acyl chains and the polar head groups. Jere P. Segrest. *Febs letters* 1976, 69 (1): 111–114.

The term "peptide" and "protein" may be used interchangeably herein. Further, the peptide analogues of the invention can be peptides, proteins or non-peptides i.e., peptidomimetics. However, all the analogues are preferably bioactive molecules.

The term "lipid" as used herein includes but is not limited to natural and synthetic phospholipids. Further, the terms, "Lipid" and "phospholipid" may be used interchangeably herein.

4. BRIEF DESCRIPTION OF THE FIGURES

FIG. 1: Superose 6 chromatography of HDL prepared by density ultracentrifugation from 200 µl human serum.

Figure 2:
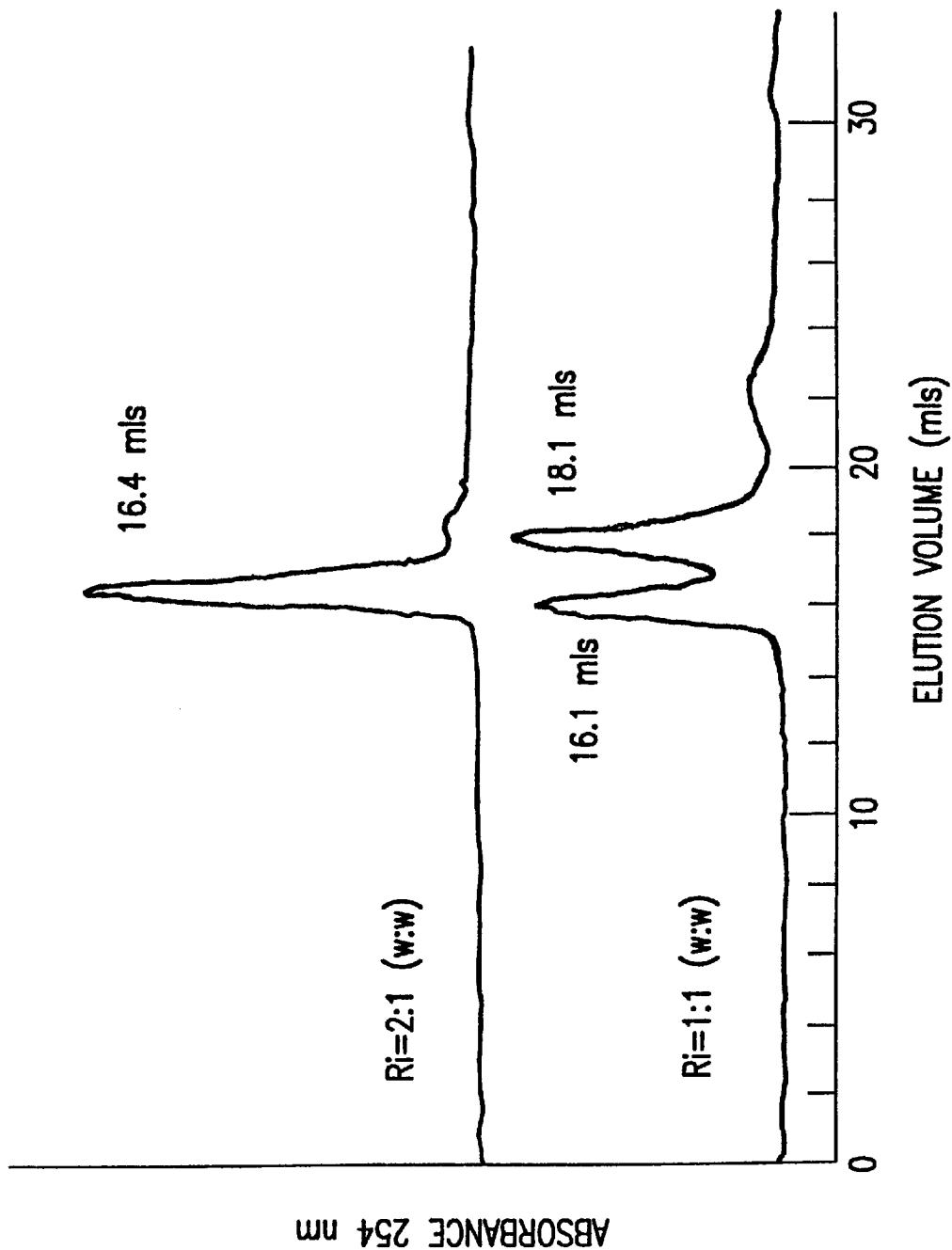

FIG. 2 (bottom): Superose 6 chromatography of (DPPC: peptide 1) (PVLDLFRELLNELLEALKQKLK; SEQ ID NO:1) complexes prepared at a ratio of 1:1 (w:w).

FIG. 2 (top): Superose 6 chromatography of (DPPC: peptide 1) complexes prepared at a ratio of 2:1 (w:w).

Figure 3:
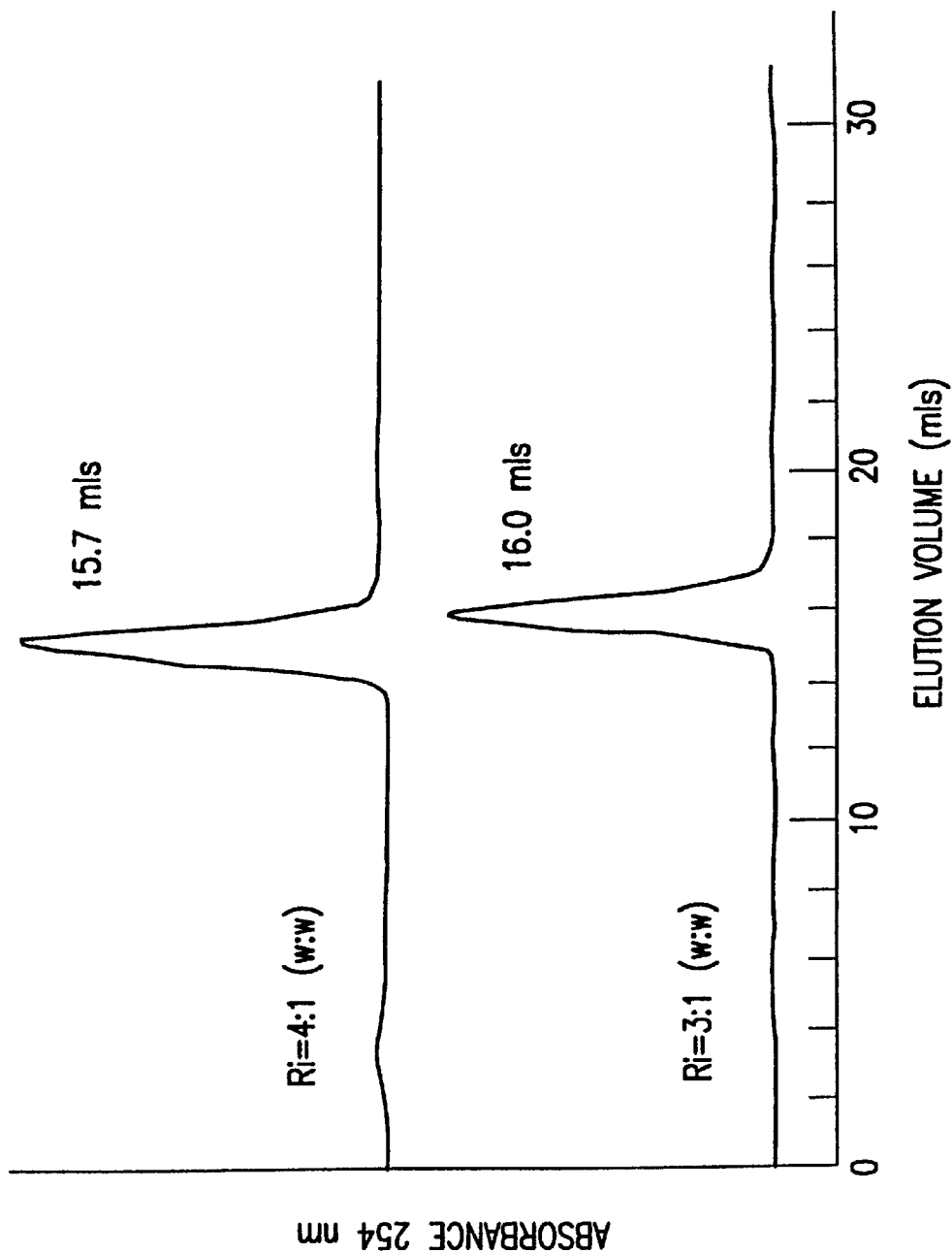

FIG. 3 (bottom): Superose 6 chromatography of (DPPC: peptide 1) complexes prepared at a ratio of 3:1 (w:w).

FIG. 3 (top): Superose 6 chromatography of (DPPC: peptide 1) complexes prepared at a ratio of 4:1 (w:w).

Figure 4:
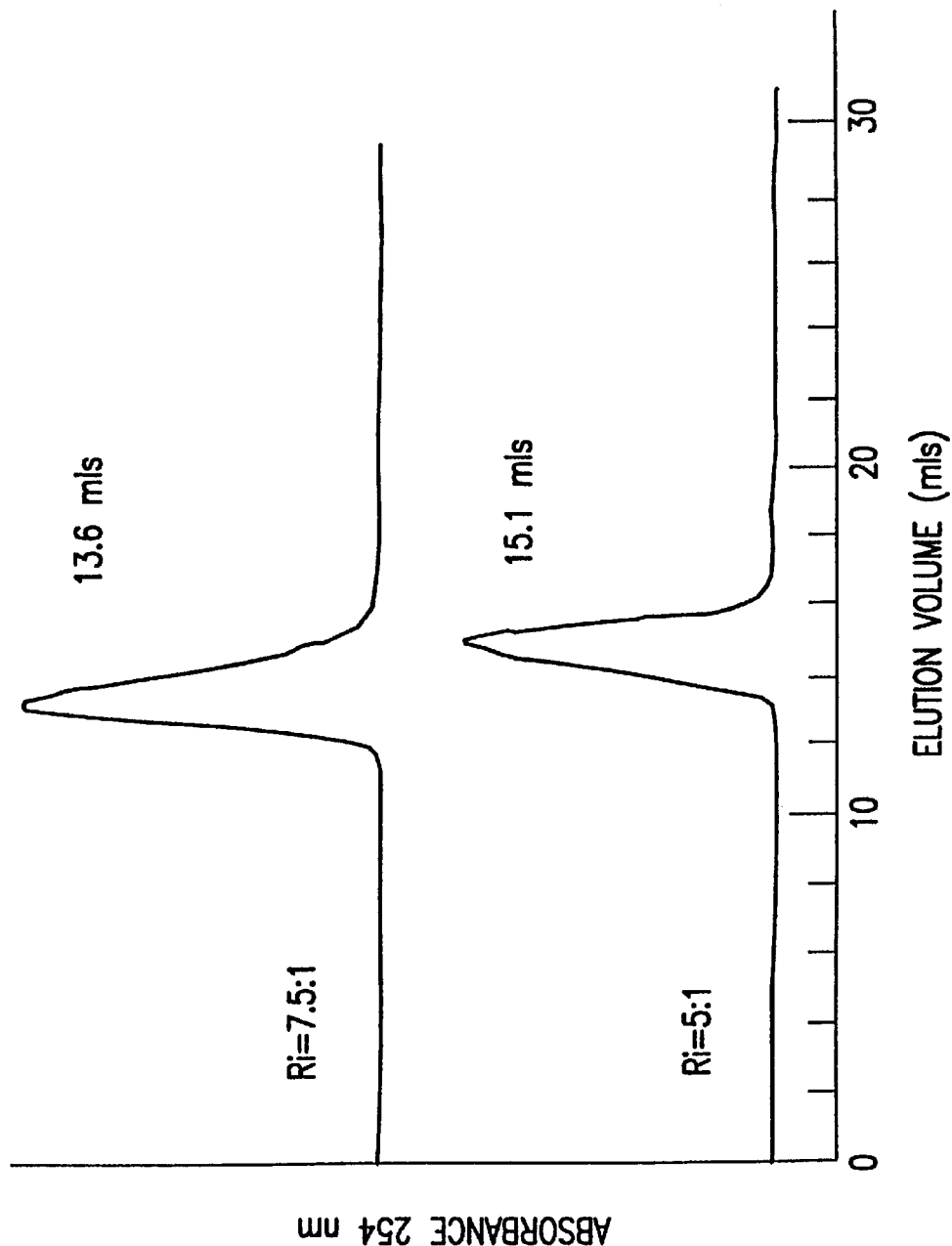

FIG. 4 (bottom): Superose 6 chromatography of (DPPC: peptide 1) complexes prepared at a ratio of 5:1 (w:w).

FIG. 4 (top): Superose 6 chromatography of (DPPC: peptide 1) complexes prepared at a ratio of 7.5:1 (w:w).

Figure 5:
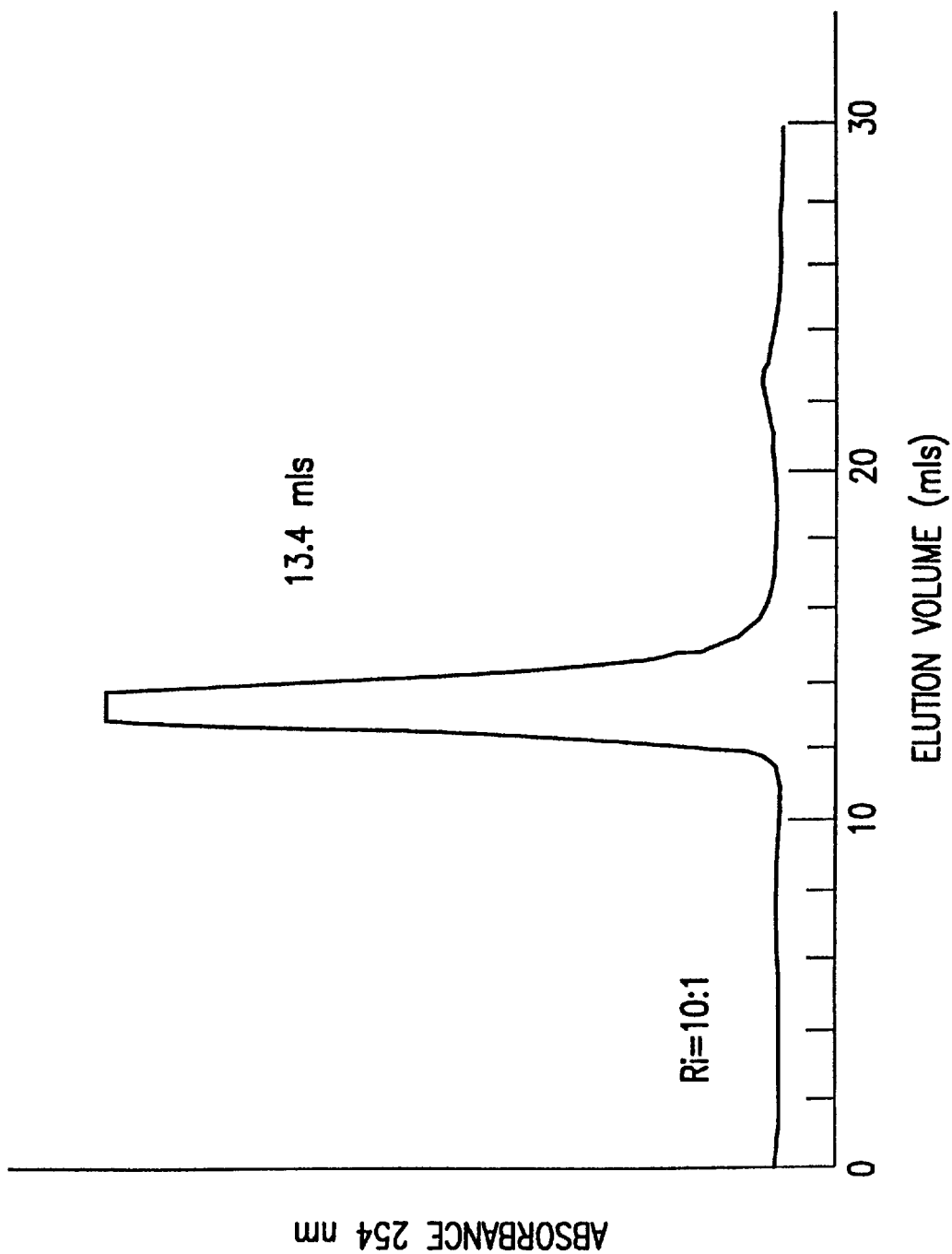

FIG. 5: Superose 6 chromatography of (DPPC: peptide 1) complexes prepared at a ratio of 10:1 (w:w).

Figure 6:
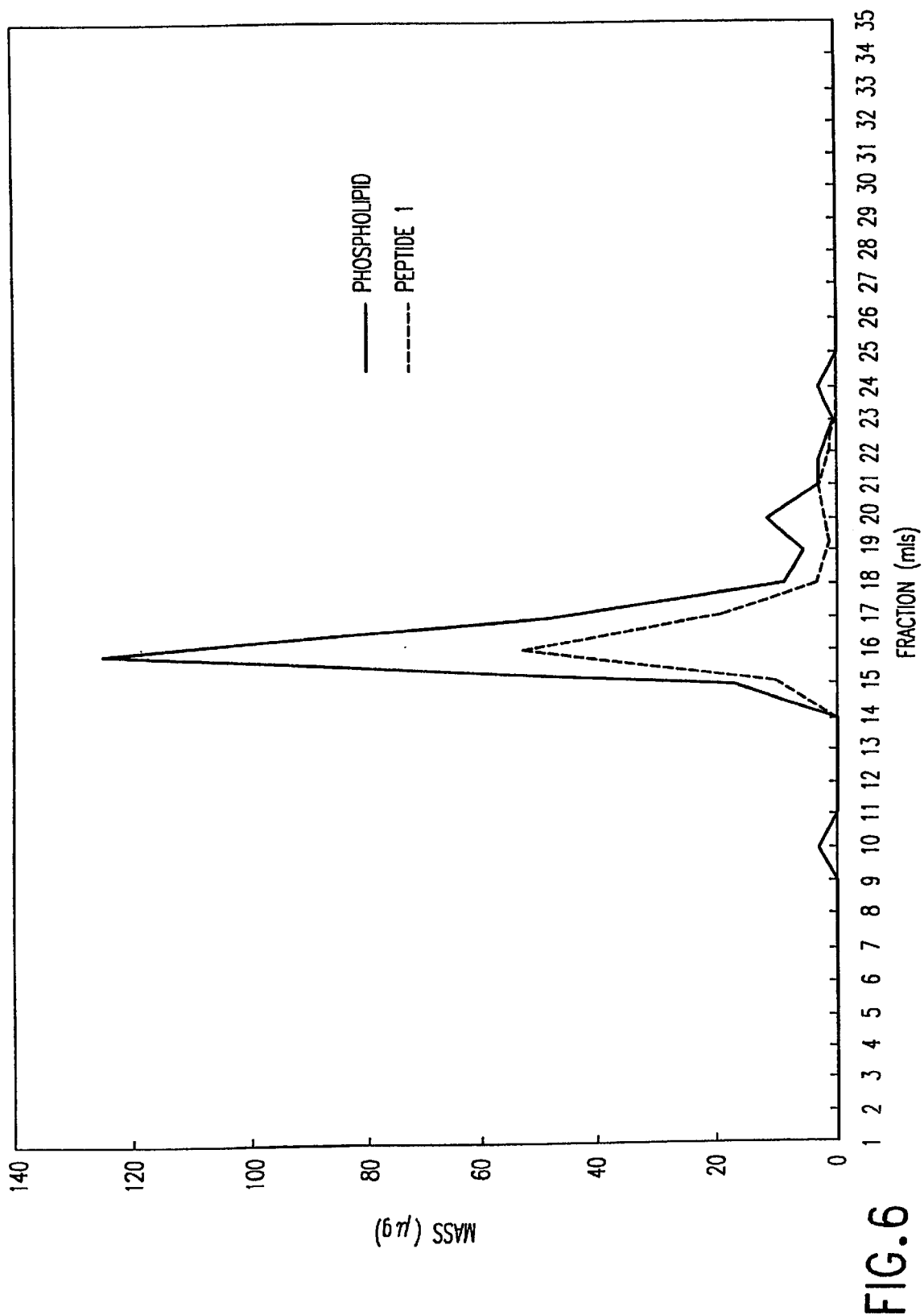

FIG. 6: Superose 6 chromatography of $^{14}$C-labeled peptide 1 complexes at Ri=3:1.

Figure 7:
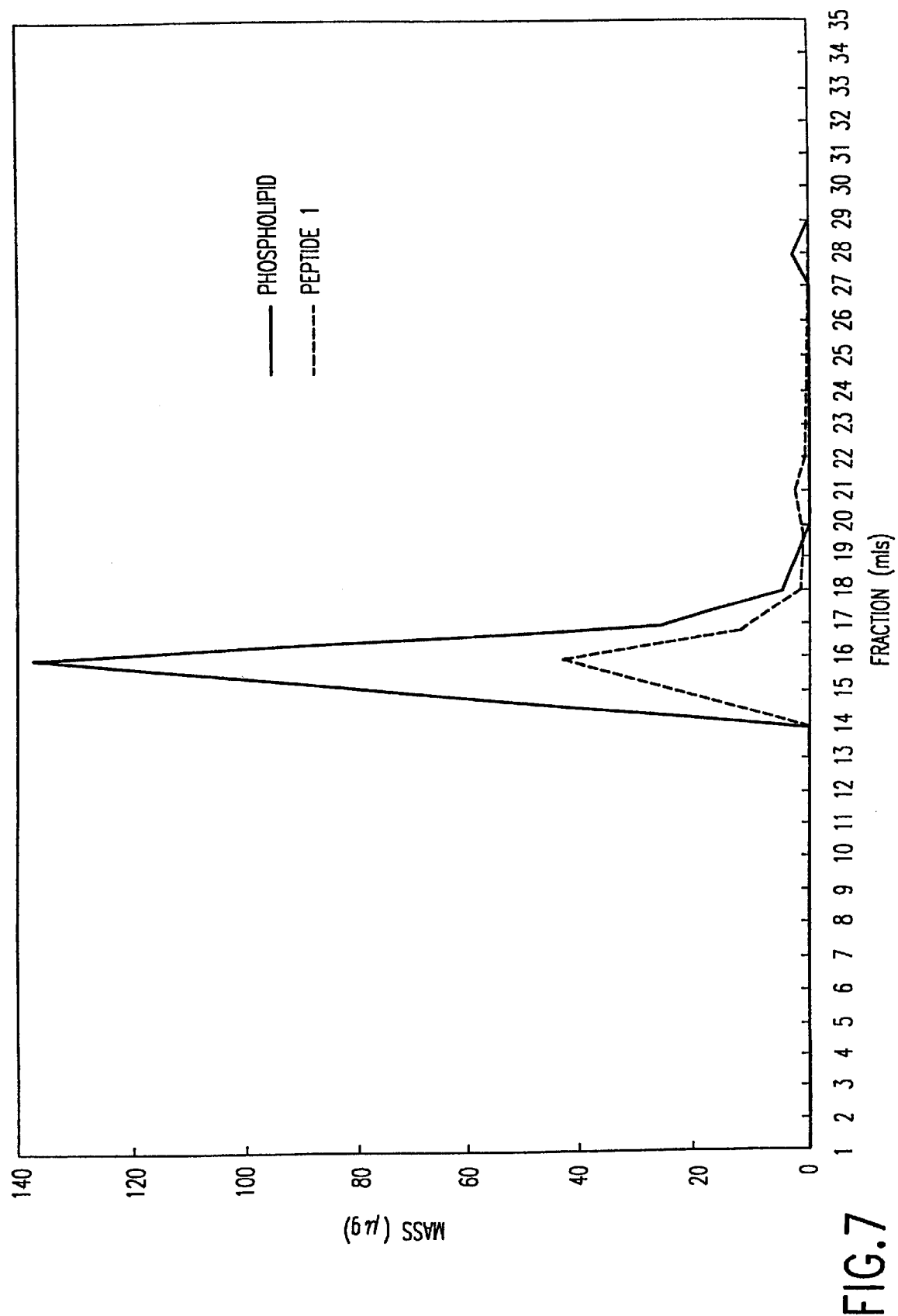

FIG. 7: Superose 6 chromatography of $^{14}$C-labeled peptide 1 complexes at Ri=4:1.

Figure 8:
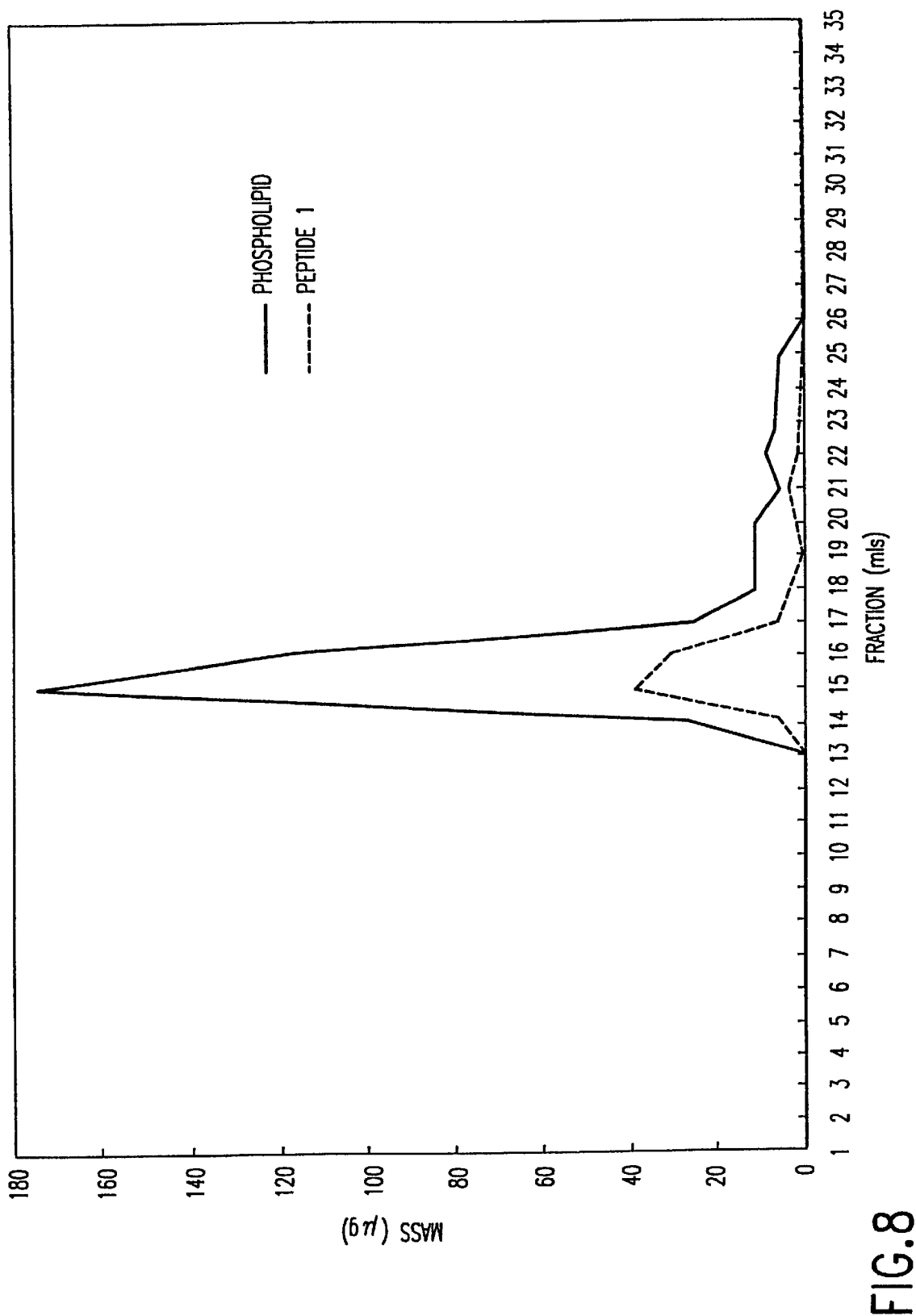

FIG. 8: Superose 6 chromatography of $^{14}$C-labeled peptide 1 complexes at Ri=5:1.

5. DETAILED DESCRIPTION OF THE PREFERRED EMBODIMENTS

The amphipathic alpha helical peptides or proteins, lipid binding proteins, ApoA-I agonist peptides, apoprotein analogues, and the like, which are useful in the present invention, can be synthesized or manufactured using any technique known in the art. Stable preparations of peptides which have a long shelf life may be made by lyophilizing the peptides—either to prepare bulk for reformulation, or to prepare individual aliquots or dosage units which can be reconstituted by rehydration with sterile water or an appropriate sterile buffered solution prior to administration to a subject.

To the inventor's knowledge, this invention is the first instance of a method for co-lyophilizing an amphipathic alpha helical peptide or peptide analogue with a lipid to form a mixture that can be reconstituted into a sterile peptide/lipid complex.

In certain embodiments, it may be preferred to formulate and administer the ApoA-I analog(s) including but not limited to ApoA-I agonists, in a peptide-lipid complex. This approach has several advantages since the complex should have an increased half-life in the circulation, particularly when the complex has a similar size and density to the HDL class of proteins, especially the pre-beta HDL populations. The HDL class of lipoproteins can be divided into a number of subclasses based on such characteristics as size, density and electrophoretic mobility. Some examples, in order of increasing size are micellar pre-beta HDL of diameter 50 to 60 Angstroms, discoidal HDL of intermediate size i.e., with a mass of 65 kDa (about 70 Angstroms), spherical HDL$_3$ or HDL$_2$ of diameter 90 to 120 Angstroms. (J. Kane, 1996 in V. Fuster, R. Ross and E. Topol [feds.] *Atherosclerosis and Coronary Artery Disease*, p. 99; A. Tall and J. Breslow, ibid., p. 106; Barrans et al., *Biochemica et Biophysica Acta* 1300, p. 73–85; and Fielding et al., 1995, *J. Lipid Res* 36, p,. 211–228). However, peptide/lipid complexes of smaller or larger size than HDL may also be formed by the invention.

The peptide-lipid complexes of the present invention can conveniently be prepared as stable preparations, having a long shelf life, by the co-lyophilization procedure described below. The lyophilized peptide-lipid complexes can be used to prepare bulk drug material for pharmaceutical reformulation, or to prepare individual aliquots or dosage units which can be reconstituted by rehydration with sterile water or an appropriate buffered solution prior to administration to a subject.

The applicants have developed a simple method for preparing peptide or protein-(phospho)lipid complexes which have characteristics similar to HDL. This method can be used to prepare the ApoA-I peptide-lipid complexes, and has the following advantages: (1) Most or all of the included ingredients are used to form the designed complexes, thus avoiding waste of starting material which is common to the other methods. (2) Lyophilized compounds are formed which are very stable during storage. The resulting complexes may be reconstituted immediately before use. (3) The resulting complexes usually do not require further purification after formation or before use. (4) Toxic compounds, including detergents such as cholate, are avoided. Moreover, the production method can be easily scaled up and is suitable for GMP manufacture (i.e., in an endotoxin-free environment).

In accordance with the preferred method, the peptide and lipid are combined in a solvent system which co-solubilizes each ingredient. To this end, solvent pairs must be carefully selected to ensure co-solubility of both the amphipathic peptide and the hydrophobic lipid. In one embodiment, the protein(s) or peptide(s) to be incorporated into the particles can be dissolved in an aqueous or organic solvent or mixture of solvents (solvent 1). The (phospho)lipid component is dissolved in an aqueous or organic solvent or mixture of solvents (solvent 2) which is miscible with solvent 1, and the two solutions are combined. Alternatively, the (phospho) lipid component is dissolved directly in the peptide (protein) solution. Alternatively, the peptide and lipid can be incorporated into a co-solvent system, i.e., a mixture of the miscible solvents. Depending on the lipid binding properties of the peptide or protein, those skilled in the art will recognize that enhanced or even complete solubilization (and/or enhanced mixing) may be necessary prior to lyophilization; thus, the solvents can be chosen accordingly.

A suitable proportion of peptide (protein) to lipids is first determined empirically so that the resulting complexes possess the appropriate physical and chemical properties, usually but not always meaning similar in size to $HDL_2$ or $HDL_3$. The lipid to protein/peptide molar ratio should be in the range of about 2 to about 200, and preferably 5 to 50 depending on the desired type of complexes. Examples of such size classes of peptide/lipid or protein/lipid complexes include, but are not limited to, micellar or discoidal particles (usually smaller than $HDL_3$ or $HDL_2$), spherical particles of similar size to $HDL_2$ or $HDL_3$ and larger complexes which are larger than HDL2. The HDLs used by us as a standard during chromatography (FIG. 1) are mainly spherical mature $HDL_2$. Pre-β1 HDL are micellar complexes of apolipoprotein and few molecules of phospholipids. Pre-β2 HDL are discoidal complexes of apolipoprotein and molecules of phospholipids. The more lipids (triglycerides, cholesterol, phospholipids) are incorporated the bigger will become the HDL and its shape is modified. (Pre-β1 HDL (micellar complex)→Pre-β2 HDL (discoidal complex))→$HDL_3$ (spherical complex)→$HDL_2$ (spherical complex).

Once the solvent is chosen and the peptide and lipid have been incorporated, the resulting mixture is frozen and lyophilized to dryness. Sometimes an additional solvent is added to the mixture to facilitate lyophilization. This lyophilized product can be stored for long periods and will remain stable.

In the working examples describe infra, the peptide 1 PVLDLFRELLNELLEALKQKLK (SEQ ID NO:1) and (phospho)lipid were dissolved separately in methanol, combined, then mixed with xylene before lyophilization. The peptide and lipid can both be added to a mixture of the two solvents. Alternatively, a solution of the peptide dissolved in methanol can be mixed with a solution of lipid dissolved in xylene. Care should be taken to avoid salting out the peptide. The resulting solution containing the peptide and lipid co-solubilized in methanol/xylene is lyophilized to form a powder.

The lyophilized product can be reconstituted in order to obtain a solution or suspension of the peptide-lipid complex. To this end, the lyophilized powder is rehydrated with an aqueous solution to a suitable volume (often about 5 mg peptide/ml which is convenient for intravenous injection). In a preferred embodiment the lyophilized powder is rehydrated with phosphate buffered saline or a physiological saline solution. The mixture may have to be agitated or vortexed to facilitate rehydration, and in most cases, the reconstitution step should be conducted at a temperature equal to or greater than the phase transition temperature (Tm) of the lipid component of the complexes. Within minutes, a solution of reconstituted lipid-protein complexes (a clear solution when complexes are small) results.

An aliquot of the resulting reconstituted preparation can be characterized to confirm that the complexes in the preparation have the desired size distribution, e.g., the size distribution of HDL. Gel filtration chromatography can be used to this end. In the working examples described infra, a Pharmacia Superose 6 FPLC gel filtration chromatography system was used. The eluant used contains 150 mM NaCl in deionized water. A typical sample volume is 20 to 200 microliters of complexes containing 5 mg peptide/ml. The column flow rate is 0.5 ml/min. A series of proteins of known molecular weight and Stokes' diameter as well as human HDL are used as standards to calibrate the column. The proteins and lipoprotein complexes are monitored by absorbance or scattering of light of wavelength 254 or 280 nm.

The solvents that may be used according to the method of the present invention include but are not limited to nonpolar, polar, aprotic, and protic organic solvents and the like such as ethanol, methanol, cyclohexane, 1-butanol, isopropyl alcohol, xylene, THF, ether, methylene chloride benzene and chloroform. The invention also includes the use of solvent mixtures as well as single solvents. Further, prior to use within the present methods the organic solvents maybe dried to remove water; however, hydrated solvents or water may be used with certain lipids, peptides or proteins. In other words, water may be a suitable solvent, or hydrated solvents or organic solvent/water mixtures may be used, however, if water is used it must be detergent free. As mentioned above, the solvents are preferably of the purest quality (in order to avoid concentrating impurities after lyophilization), and the solvents should be salt free and free of particulates. However, the solvents need not be sterile as the resulting product can be sterilized before, during or after lyophilization, in accordance with known techniques in the pharmaceutical art, such as those described in Remington's Pharmaceutical Sciences, 16th and 18th Eds., Mack Publishing Co., Easton, Pa. (1980 and 1990), herein incorporated by reference in its entirety, and in the United States Pharmacopeia/National Formulary (USP/NF) XVII, herein incorporated by reference in its entirety.

The lipids which may be used according to the method of the present composition include but are not limited to natural and synthesized (synthetic) lipids and phospholipids including small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, sphingomyelin sphingolipids, phosphatidylglycerol, diphosphatidylglycerol dimyristoylphosphatidylglycerol, dipalmitoylphosphatidylglycerol, distearoylphosphatidylglycerol, dioleoylphosphatidylglycerol, dimyristoylphosphatidic acid dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio)hexyl ether glycolipids, and cholesterol and its derivatives.

The peptides that are suitable for use with the present Ser. No. 08/940,095, filed Sep. 29, 1997, now Pat. No. 6,004,925; Ser. No. 08/940,096, filed Sep. 29, 1997, now Pat. No. 6,046,166; and Ser. No. 08/940,093, filed Sep. 29, 1997, now Pat. No. 6,037,323, each of which is rated by reference in its entirety.

It is preferred, although not necessary in every case, that precipitates should be solubilized or removed prior to mixing or stirring the lipid and peptide solutions or prior to lyophilization.

The method may be used for large scale production of peptide/lipid complexes, amphipathic peptide/(phospho) lipid complexes, lipid binding protein/(phospho)lipid complexes, and/or ApoA1 peptide analogue/(phospho)lipid complexes. The lyophilized material may be prepared for bulk preparations, or alternatively, the mixed peptide/lipid solution may be apportioned in smaller containers (for example, single dose units) prior to lyophilization, and such smaller units may be prepared as sterile single dosage forms.

The vacuum dried compositions of the present invention may be provided in single dose or multiple dose container forms by aseptically filling suitable containers with the sterile pre-vacuum dried solution to a prescribed content; preparing the desired vacuum dried compositions; and then hermetically sealing the single dose or multiple dose container. It is intended that these filled containers will allow rapid dissolution of the dried composition upon reconstitution with appropriate sterile diluents in situ giving an appropriate sterile solution of desired concentration for administration. As used herein, the term "suitable containers" means a container capable of maintaining a sterile environment, such as a vial, capable of delivering a vacuum dried product hermetically sealed by a stopper means. Additionally, suitable containers implies appropriateness of size, considering the volume of solution to be held upon reconstitution of the vacuum dried composition; and appropriateness of container material, generally Type I glass. The stopper means employed, e.g., sterile rubber closures or the equivalent, should be understood to be that which provides the aforementioned seal, but which also allows entry for the purpose of the introduction of a diluent, e.g., sterile Water for Injection, USP, Normal Saline, USP, or 5% Dextrose in Water, USP, for the reconstitution of the desired solution. These and other aspects of the suitability of containers for pharmaceutical products such as those of the instant invention are well known to those skilled in the practice of pharmaceutical arts. In specific embodiments, sizes of product unit dosages may be in a range of about 10 mg to 2 g of peptide preferably in the range of about 100 mg to 1 g and at a concentration after reconstitution of about 1 to 50 mg/ml, preferably about 2 to 25 mg/ml.

The method of the invention enables the preparation of protein or peptide/lipid complexes for parenteral administration including intravenous, intraperitoneal, subcutaneous, intramuscular and bolus injections to animals or humans, or for oral, rectal, mucosal (e.g. oral cavity) or topical administration to animals or humans, or for in vitro experimentation.

The lyophilized powder prepared by the method of the invention can be rehydrated immediately before injection, or alternatively, the lyophilized powder can be administered directly. The lyophilized powder includes, but is not limited to lipid and peptides that are able to form complexes in the form of vesicles, liposomes, particles including spherical or discoidal particles, micelles and the like. In order to reconstitute or rehydrate the lyophilized powder a solution is chosen depending upon the desired end use. For pharmaceutical use any sterile solution may be used. Further, buffered solutions are preferred for certain uses and these include but are not limited to phosphate, citrate, tris, baribital, acetate, glycine-HCl, succinate, cacodylate, boric acid-borax, ammediol and carbonate.

The lyophilized powder of the present invention may be formed using any method of lyophilization known in the art, including, but not limited to, freeze-drying in which the peptide/lipid-containing solution is subjected to freezing followed by reduced pressure evaporation.

The method may also be suitable for storage of compounds which may be otherwise unstable or insoluble in the absence of lipids.

The method may be used for the formulation of products for the treatment or prevention of human diseases, including such applications as co-presentation of antigens in vaccines, treatment or prevention of dyslipoproteinemias including but not limited to hypercholesterolemia, hypertriglyceridemia, low HDL, and apolipoprotein A-1 deficiency, cardiovascular disease such as atherosclerosis, septic shock, or infectious diseases.

The method may be used for the preparation of complexes that could be used as carriers for drugs, as vectors (to deliver drugs, DNA, genes), for example, to the liver or to extrahepatic cells, or as scavengers to trap toxin (e.g. pesticides, LPS, etc.). Alternatively, the method may be used to prepare complexes for in vitro assay systems, or for use in imaging technology.

In specific embodiments, the method may be used for the preparation of ApoA-I analogue (including but not limited to agonists) complexes which may be used in in vitro diagnostic assays and as markers for HDL populations and subpopulations. In other specific embodiments, ApoA-I agonist complexes may be used for immunoassays or for imaging technology (e.g., CAT scans, MRI scans).

The following examples are intended to be illustrative of the present invention and should not be construed, in any way, to be a limitation thereof.

6. EXAMPLE

Reparation of Peptide Lipid Complex by Co-Lyphilization Approach

The following protocol was utilized to prepare peptide-lipid complexes.

Peptide 1 (PVLDLFRELLNELLEALKQKLK; SEQ ID NO:1) (22.4 mg) was dissolved in methanol at a concentration of 3.5 mg/ml by incubation for several minutes and mixing by vortex intermittently. To this solution was added dipalmitoylphosphatidylcholine (DPPC) in methanol (100 mg/ml stock solution) such that the final ratio of DPPC/peptide was 2.5:1 (weight/weight). This solution was mixed by vortexing. Xylene was added to the solution to a final concentration of 36%. Aliquots of the resulting solution were removed for later analysis by gel filtration chromatography. The solutions were frozen in liquid nitrogen and lyophilized to dryness by vacuum. An aliquot containing 20 mg peptide 1 (SEQ ID NO:1) and 50 mg DPPC was rehydrated in sterile saline solution (0.9% NaCl), mixed, and heated to 41° C. for several minutes until a clear solution of reconstituted peptide/phospholipid complexes resulted.

6.1. Example

Gel Filtration and Phospholipid Utilization

6.1.1. Materials and Methods

For the purpose of testing conditions for the preparation of complexes it is often convenient to prepare small amounts of complexes for characterization. These preparations contained one mg of peptide and were prepared as follows: One mg of peptide 1 (SEQ ID NO: 1) was dissolved in 250 µl HPLC grade methanol (Perkin Elmer) in a 1.0 ml clear glass vial with cap (Waters #WAT025054). Dissolving of the peptide was aided by occasional vortexing over a period of 10 minutes at room temperature. After this time a small amount of undissolved particulate matter could still be seen but this did not adversely affect the results. To this mixture an aliquot containing either 1, 2, 3, 4, 5, 7.5, 10 or 15 mg DPPC (Avanti Polar Lipids, 99% Purity, product #850355) from a 100 mg/ml stock solution in methanol was added. The volume of the mixture was brought to 400 µl by addition of methanol and the mixture was further vortexed intermittently for a period of 10 minutes at room temperature. At this time, very little undissolved material could be seen in the tubes. To each tube 200 µl of xylene (Sigma-Aldrich 99% pure, HPLC-grade) was added and the tubes were vortexed for 10 seconds each. Two small holes were punched into the tops of each tube with a 20 gauge syringe needle, the tubes were frozen for 15 seconds each in liquid nitrogen, and the tubes were lyophilized overnight under vacuum. To each tube 200 ml of 0.9% NaCl solution was added. The tubes were vortexed for 20 seconds each. At this time the solutions in the tubes were milky in appearance. The tubes were then incubated in a water bath for 30 minutes at 41° C. The solutions in all of the tubes became clear (i.e., similar to water in appearance) except for the tube containing 15 mg DPPC, which remained milky.

In order to determine if all of the phospholipids that were used in the complex preparations actually appeared in the column fractions corresponding to the chromatogram absorbance peaks, the column eluate from reconstituted peptide/lipid complexes was collected in one or two ml fractions and the fractions were assayed enzymatically for phospholipid content with the BioMerieux Phospholipides Enzymatique PAP 150 kit (#61491) according to the instructions supplied by the manufacturer.

The preparations of complexes may also be done on a larger scale. An example of one such preparation is reported above. These complexes were used for in vivo experiments.

6.2. Results of Complex Characterization

FIG. 1: Superose 6 chromatography of mature $HDL_2$ prepared by density ultracentrifugation from 200 µl human serum. Chromatograph shows absorbance at 254 nm. Elution volume 14.8 ml, corresponding to a Stokes' diameter of 108 Angstroms (See Table 1).

FIG. 2 (bottom): Superose 6 chromatography of DPPC:peptide 1 complexes prepared at a ratio of incubation (Ri, defined as the ratio of total phospholipid to total peptide in starting mixture) of 1:1 (w:w) as described above (small scale preparation). Elution volumes of absorbance peaks= 16.2 mls and 18.1 ml corresponding to particles of Stokes' diameters 74 and 82 Angstroms, which are smaller than HDL. 87% of the phospholipid applied to the column was recovered in the fractions containing the absorbance peaks (See Table 1).

FIG. 2 (top): Superose 6 chromatography of DPPC:peptide 1 complexes prepared at an Ri of 2:1 (w:w) as described above. Elution volume of absorbance peak=16.4 ml, (77 Angstroms), corresponding to particles smaller than HDL. 70% of the phospholipid applied to the column was recovered in the fractions containing the absorbance peak (See Table 1).

FIG. 3 (bottom): Superose 6 chromatography of DPPC:peptide 1 complexes prepared at an Ri of 3:1 (w:w) as described above. Elution volume of absorbance peak= 16.0 ml, (80 Angstroms) corresponding to particles smaller than HDL. 79% of the phospholipid applied to the column was recovered in the fractions containing the absorbance peak (See Table 1).

FIG. 3 (top): Superose 6 chromatography of DPPC:peptide 1 complexes prepared at an Ri of 4:1 (w:w) as described above. Elution volume of the absorbance peak=15.7 ml, (90 Angstroms), corresponding to particles smaller than HDL. 106% of the phospholipid applied to the column was recovered in the fractions containing the absorbance peak (See Table 1).

FIG. 4 (bottom): Superose 6 chromatography of DPPC:peptide 1 complexes prepared at an Ri of 5:1 (w:w) as described above. Elution volume of the absorbance peak= 15.1 ml, (104 Angstroms), corresponding to particles smaller than HDL. 103% of the phospholipid applied to the column was recovered in the fractions containing the absorbance peak (See Table 1).

FIG. 4 (top): Superose 6 chromatography of DPPC:peptide 1 complexes prepared at an Ri of 7.5:1 (w:w) as described above. Elution volume of the absorbance peak= 13.6 ml, (134 Angstroms) corresponding to particles larger than HDL. 92% of the phospholipid applied to the column was recovered in the fractions containing the absorbance peaks (See Table 1).

FIG. 5: Superose 6 chromatography of DPPC:peptide 1 complexes prepared at a ratio of 10:1 (w:w) as described above. Elution volume of absorbance peak=13.4 ml, (138 Angstroms), again corresponding to particles larger than HDL. 103% of the phospholipid applied to the column was recovered in the fractions containing the absorbance peaks (See Table 1).

The sample containing complexes with 15:1 DPPC:peptide 1 (w:w) was not subjected to Superose 6 chromatography because it was turbid, suggesting the presence of large particles.

For each of the above experiments, no significant phospholipid was observed in any fraction other than those containing material eluting with the absorbance peaks (See FIGS. 2–8). This suggests that virtually all of the phospholipids (within experimental error of the assay) were incorporated into the complexes. The experiment demonstrates that by varying the initial ratio of phospholipids to peptides, homogeneous complexes of various sizes (smaller or larger than HDL) can be formed.

6.3. Characterization of Complexes Using $^{14}C$-Labeled Peptide 1

Peptide-phospholipid complexes containing $^{14}C$-labeled peptide 1 (specific activity 159,000 DPM/mg peptide by weight, assuming 50% peptide content) were prepared by co-lyophilization as described above. The preparations each contained 1 mg peptide and 3, 4 or 5 mg DPPC by weight. After reconstituting the complexes in 200 µl 0.9% NaCl, 20 µl (100 µg) of the complexes were applied to a Pharmacia Superose 6 column using 0.9% NaCl as the liquid phase at a flow rate of 0.5 ml/min. After a 5 ml delay (column void volume=7.7 ml) 1 ml fractions were collected. Aliquots containing 20 μl of the fractions were assayed for phospholipid content using the BioMerieux enzymatic assay. The remainder of each fraction was counted for 3 minutes in a Wallach 1410 liquid scintillation counter (Pharmacia) using the Easy Count program. The results of these analyses are shown in FIGS. 6–8. It can be seen that the vast majority of both phospholipid and peptide are recovered together in a few fractions with peaks at approximately 16, 16, and 15 ml for complexes prepared at 3:1, 4:1 and 5:1 DPPC:peptide ratios, respectively. The UV absorbance profiles for these samples indicate that the complexes elute from the column at volumes 15.1, 14.7 and 14.4 ml for complexes prepared at 3:1, 4:1 and 5:1 DPPC:peptide ratios, respectively (the dead volume of tubing between the fraction collector and UV flow cell is 1.3 ml, which explains a slight discrepancy between the elution volumes as measured by radioactivity/phospholipid assay and UV absorbance). The elution volumes correspond to Stoke's diameters of 106, 114, and 120 Angstroms for the 3:1, 4:1 and 5:1 Ri complexes, respectively.

TABLE 1

| DPPC: Peptide 1 ratio | Elution Volume | Relative Size of Particles* | % of Applied Phospholipid in Absorbance Peak |
|---|---|---|---|
| HDL | 14.8 | — | — |
| 1:1 | 16.2 and 18.1 | Smaller | 87% |
| 2:1 | 16.4 | Smaller | 70% |
| 3:1 | 16.0 | Smaller | 79% |
| 4:1 | 15.7 | Smaller | 106% |
| 5:1 | 15.1 | Smaller | 103% |
| 7.5:1 | 13.6 | Larger | 92% |
| 10:1 | 13.4 | Larger | 103% |
| 15:1 | ND** | ND | ND |

*Relative to size of HDL particles
**ND, not done

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

I claim:

1. A method of preparing a lyophilized peptide/lipid product consisting essentially of co-lyophilizing one or more peptides or peptide analogues, which are able to adopt an amphipathic conformation, and one or more lipids in a solvent system to form a peptide/lipid product, wherein said product can be rehydrated to form peptide/lipid complexes, and wherein said solvent is an organic solvent or an aqueous/organic solvent mixture.

2. A method of preparing a lyophilized peptide/lipid product consisting essentially of lyophilizing a solubilized solution comprising a peptide or peptide analogue capable of adopting an amphipathic conformation, a lipid, and a solvent, wherein said lipid is dissolved in said solution without the aid of a detergent, wherein said lyophilized product can be rehydrated to form a peptide/lipid complex, and wherein said solvent is an organic solvent, or an aqueous/organic solvent mixture.

3. The method of claim 2 wherein the solvent is nonpolar, polar, aprotic or protic.

4. The method of claim 2 wherein the solvent is ethanol, methanol, cyclohexane, 1-butanol, isopropyl alcohol, xylene, THF, ether, methylene chloride, benzene or chloroform.

5. The method of claim 2 wherein the solvent is a mixture of ethanol, methanol, cyclohexane, 1-butanol, isopropyl alcohol, xylene, THF, ether, methylene chloride, benzene or chloroform, and water.

6. The method of claim 2 wherein said peptide is a protein.

7. The method of claim 2 wherein said peptide is a lipid binding protein.

8. The method of claim 2 wherein said peptide analogue is an analogue of ApoA-I, ApoA-II, ApoA-IV, ApoC-I, ApoC-II, ApoC-III or ApoE.

9. The method of claim 2 wherein said lipid is a saturated lipid, unsaturated lipid, or mixtures thereof.

10. The method of claim 2, further comprising aliquoting said peptide/lipid solution into individual containers before lyophilization to form a single unit dosage form.

11. The method of claim 2 which further comprises sterilizing said product prior to, during or after lyophilization.

12. The method of claim 2 wherein said lipid is a natural lipid, synthetic lipid, or mixtures thereof.

13. The method of claim 12 wherein said lipid is selected from the group consisting of ether phospholipids, short chain phospholipids, cholesterol, cholesterol derivatives, phosphatidylcholines, phosphatidylethanolamines, phosphatidylserines, phosphatidylinositols, sphingolipids, phosphatidylglycerols, gangliosides, and cerebrosides.

14. The method of claim 13 wherein said lipid is selected from the group consisting of egg phosphatidylcholine, soybean phosphatidylcholine, dipalmitoylphosphatidylcholine, dimyristoylphosphatidylcholine, distearoylphosphatidylcholine, 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine, dioleophosphatidylethanolamine, dilauroylphosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, sphingomyelin, dipalmitoylsphingomyelin, distearoylsphingomyelin, phosphatidic acid, galactocerebroside, dilaurylphosphatidylcholine, (1,3)-D-mannosyl(1,3) diglyceride, aminophenylglycoside, 3-cholesteryl-6'-(glycosylthio)hexyl ether glycolipids and mixtures thereof.

15. The method of claim 14 wherein said lipid is a 3-cholesteryl-6α-(glycosylthio)hexyl ether glycolipid.

16. A method of preparing a lyophilized peptide/lipid product, which can be rehydrated to form a peptide/lipid complex, consisting essentially of:

(i) solubilizing at least one amphipathic peptide or amphipathic peptide analogue in a first solvent to form a first solution;

(ii) solubilizing at least one lipid in a second solvent without the aid of detergent to form a second solution, wherein said second solution is miscible with said first solution;

(iii) combining said first solution with said second solution to form a solubilized peptide/lipid solution; and (iv) lyophilizing said peptide/lipid solution to form a lyophilized peptide/lipid product;

wherein the first solvent and the second solvent are an organic solvent or aqueous/organic solvent mixture.

17. The method of claim 16 wherein said peptide is a protein.

18. The method of claim 16 wherein said peptide is a lipid binding protein.

19. The method of claim 16 wherein said peptide analogue is an analog of ApoA-I, ApoA-II, ApoA-IV, ApoC-I, ApoC-II, ApoC-III or ApoE.

20. The method of claim 16 wherein said lipid is a saturated lipid, unsaturated lipid, or mixtures thereof.

21. The method of claim 16 in which the first and second solvents are the same.

22. The method of claim 16 further comprising aliquoting said peptide/lipid solution into individual containers before lyophilization to form a single unit dosage form.

23. The method of claim 16 which further comprises a sterilization step prior to, during or after lyophilization.

24. The method of claim 16 wherein said lipid is a natural lipid, a synthetic lipid, or mixtures thereof.

25. The method of claim 24 wherein said lipid is selected from the group consisting of ether phospholipids, short-chain phospholipids, cholesterol, cholesterol derivatives, phosphatidylcholines, phosphatidylethanolamines, phosphatidylserines, phosphatidylinositols, sphingolipids, phosphatidylglycerols, gangliosides, and cerebrosides.

26. The method of claim 25 wherein said lipid is selected from the group consisting of egg phosphatidylcholine, soybean phosphatidylcholine, dipalmitoylphosphatidylcholine, dimyristoylphosphatidylcholine, distearoylphosphatidylcholine, 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine, dioleophosphatidylethanolamine, dilauroylphosphatidylglycerol, diphosphatidylglycerol, dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolarnine, dipalmitoylphosphatidylethanolamine, dimyristoylphosphatidylserine, dipalmitoylphosphatidylserine, sphingomyelin, dipalmitoylsphingomyelin, distearoylsphingomyelin, phosphatidic acid, galactocerebroside, dilaurylphosphatidylcholine, (1,3) -D-mannosyl(1,3) diglyceride, aminophenylglycoside, 3-cholesteryl-6'-(glycosylthio)hexyl ether glycolipids and mixtures thereof.

27. The method of claim 26 wherein said lipid is a 3-cholesteryl-6α-(glycosylthio)hexyl ether glycolipid.

* * * * *